United States Patent
Bannasch et al.

(10) Patent No.: US 10,580,171 B2
(45) Date of Patent: Mar. 3, 2020

(54) METHOD FOR DETERMINING A PERFUSION DATA SET

(71) Applicant: SIEMENS HEALTHCARE GMBH, Erlangen (DE)

(72) Inventors: Sebastian Bannasch, Magdeburg (DE); Robert Frysch, Magdeburg (DE); Georg Rose, Magdeburg (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/728,810

(22) Filed: Oct. 10, 2017

(65) Prior Publication Data

US 2018/0101968 A1 Apr. 12, 2018

(30) Foreign Application Priority Data

Oct. 11, 2016 (DE) .................. 10 2016 219 709

(51) Int. Cl.
*G06T 11/00* (2006.01)
*G06T 19/00* (2011.01)
(Continued)

(52) U.S. Cl.
CPC ............ *G06T 11/005* (2013.01); *A61B 6/486* (2013.01); *A61B 6/507* (2013.01); *G06T 15/08* (2013.01); *G16H 40/63* (2018.01); *G16H 50/50* (2018.01); *A61B 6/032* (2013.01); *A61B 6/4441* (2013.01); *A61B 6/504* (2013.01); *G06T 2200/04* (2013.01); *G06T 2211/424* (2013.01); *G06T 2215/16* (2013.01)

(58) Field of Classification Search
CPC ......... A61B 6/504; A61B 6/032; A61B 6/466; A61B 8/0891; G06T 2207/10081; G06T 15/08; G06T 2200/04

See application file for complete search history.

(56) References Cited

U.S. PATENT DOCUMENTS

| 2007/0009080 A1* | 1/2007 | Mistretta ............... G06T 11/006 378/4 |
| 2014/0126685 A1* | 5/2014 | Deuerling-Zheng ........................ A61B 6/4441 378/4 |

FOREIGN PATENT DOCUMENTS

WO    WO2005087107 A1    9/2005

OTHER PUBLICATIONS

Neukirchen, Christoph. "An extended temporal interpolation approach for dynamic object reconstruction," 11th International Meeting on Fully Three-Dimensional Image Reconstruction in Radiology and Nuclear Medicine, pp. 379-382. (Year: 2011).*
Goloub, G. H. et. al.: "Matrix Computations", The Johns Hopkins University Press, Baltimore and London; pp. 1-723 (1996).
(Continued)

*Primary Examiner* — Kenny A Cese
(74) *Attorney, Agent, or Firm* — Lempia Summerfield Katz LLC

(57) ABSTRACT

A method and system are provided for determining a time-dependent, three-dimensional perfusion data set relating to the perfusion of at least one vessel and/or of tissue of an examination object. Projection images of the vessel and/or tissue are acquired in a plurality of recording geometries by an X-ray detector at a plurality of recording times in each case, which images describe detected intensities in a plurality of imaging regions of the X-ray detector. The perfusion data set is determined by associating a weighted sum of specified time-dependent base functions with each voxel of the perfusion data set.

20 Claims, 1 Drawing Sheet

(51) Int. Cl.
*G06T 15/08* (2011.01)
*A61B 6/00* (2006.01)
*G16H 50/50* (2018.01)
*G16H 40/63* (2018.01)
*A61B 6/03* (2006.01)

(56) References Cited

OTHER PUBLICATIONS

Natterer, et al., "Mathematical Methods in Image Reconstruction," Society for Industrial and Applied Mathematics, Abstract, Retrieved from http://www.ec-securehost.com/SIAM/MM05.html; 2001.

Neunkirchen C. et. al.: "An iterative method for tomographic x-ray perfusion estimation in a decomposition model-based approach", Med Phys, 37 (12), pp. 6125-6141; Dec. 2010.

Neunkirchen C. et. al.: "Parameter Estimation in a Model Based Approach for Tomographic Perfusion Measurement", Proc. NSS-MIC (Nuclear Science Symposium and Medical Imaging Conference), Puerto Rico, 2005.

Serowy S. et. al.: "A Jacobi-like Solution to the Model Based Tomographic X-Ray Perfusion Imaging", 2007 IEEE Nuclear Science Symposium Conference Record, Proc. NSS-MIC, Hawaii, pp. 3085-3088; 2007.

Thorsten M. Buzug; Computed Tomography: From Photon Statistics to Modern Cone-Beam CT, Springer-Verlag, Berlin/Heidelberg. Chapter 4: Fundamentals of Signal Processing; 2008.

Thorsten M. Buzug; Computed Tomography: From Photon Statistics to Modern Cone-Beam CT, Springer-Verlag, Berlin/Heidelberg. Chapter 9: Image Quality and Artifacts; 2008.

Neukirchen, Christoph. "An extended temporal interpolation approach for dynamic object reconstruction," 11th International Meeting on Fully Three-Dimensional Image Reconstruction in Radiology and Nuclear Medicine, pp. 379-382 (2011).

* cited by examiner

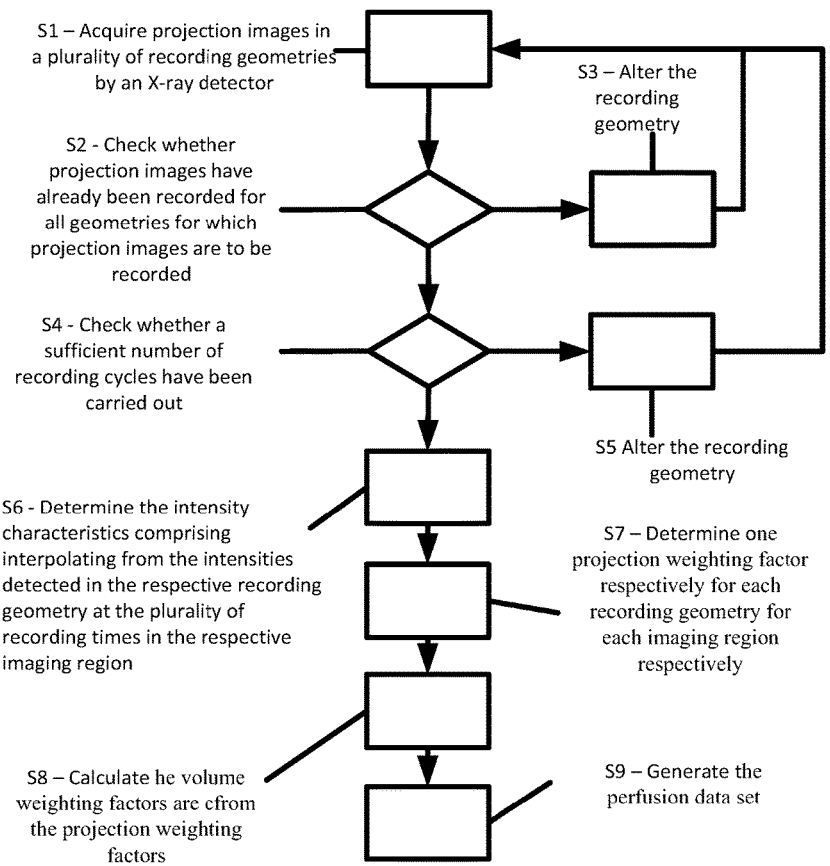
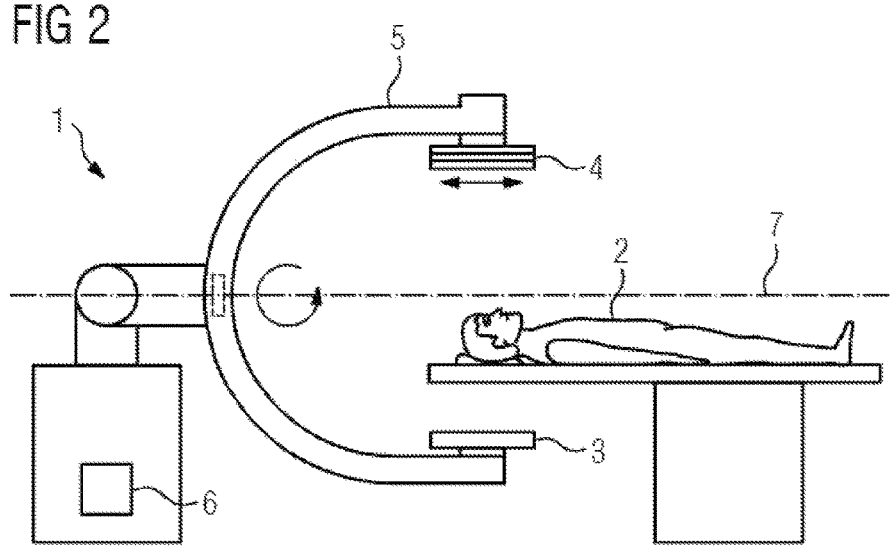

METHOD FOR DETERMINING A PERFUSION DATA SET

CROSS REFERENCE TO RELATED APPLICATIONS

This application claims the benefit of DE 102016219709.6, filed on Oct. 11, 2016, which is hereby incorporated by reference in its entirety.

FIELD

Embodiments relate to a method for determining a time-dependent, three-dimensional perfusion data set relating to the perfusion of at least one vessel and/or of tissue of an examination object.

BACKGROUND

Perfusion in vessels or tissues may be detected by X-ray methods by injecting a contrast medium and detecting the time characteristic of the contrast medium concentration as a function of location. In order to acquire three-dimensional X-ray data sets, an examination object may be recorded from a plurality of recording angles and a volume data set may be reconstructed from the projection images. Numerous methods are known, for example a back projection of the projection images. If a condition of the examination object is anticipated to change of time, as is the case with perfusion scans owing to the changing contrast medium concentration, the reconstruction takes into account that the condition of the object changes over time between the individual projection images. Although different reconstruction options are known that take account of the change, a problem is that the time resolution of a corresponding scan is typically limited by the frequency of the recording of projection images in the individual recording geometries. The limitation inevitably results from the Nyquist-Shannon sampling theorem as long as prior knowledge about the system is not used.

The result is that for perfusion data acquisition, that uses a direct reconstruction, only X-ray devices that enable acquisition of projection images from a large number of recording angles in a very fast temporal sequence are suitable. If, however, acquisition of perfusion data is possible by way of a C-arm X-ray device, then sufficiently high recording rates are not attained.

To overcome corresponding limitations, prior knowledge about the examination object being monitored may be used, for example over the course of time of the contrast medium concentration within the context of perfusion scans. WO 2005/087 107 A1 discloses describing a time characteristic of the values of the individual voxels by way of a model function that is parameterized by location-dependent parameters. The parameters are determined by an iterative method.

One problem in the connection is that appropriate iterative methods are very computing-intensive and may include additional steps have to be taken to provide convergence or stability of the method.

SUMMARY AND BRIEF DESCRIPTION

Embodiments provide an efficient option of indicating prior knowledge during the course of acquisition and/or reconstruction of a time-dependent, three-dimensional perfusion data set.

The scope of the present invention is defined solely by the appended claims and is not affected to any degree by the statements within this summary. The present embodiments may obviate one or more of the drawbacks or limitations in the related art.

Embodiments provide a method where a projection weighting factor is determined for the imaging regions for each recording geometry and each base function respectively. The projection weighting factors are determined for a respective recording geometry as a function of intensity characteristics as a function of time for the imaging regions and of the base functions. The intensity characteristics are determined by interpolation from the intensities detected in the recording geometry at the various recording times in the respective imaging region, according to which the volume weighting factors are calculated as a function of the projection weighting factors of all recording geometries and of imaging rules describing the recording geometries.

In an embodiment, the individual recording geometries are initially considered separately from each other to determine the corresponding projection weighting factors for the respective recording geometry. Compared to direct determination, the consideration significantly reduces the complexity of the problem to be solved. The reduction in complexity is achieved by the combination of two approaches. The intensities in the individual imaging regions depend on a continuous process, for example, on an increase and a decrease in a contrast medium concentration in the X-rayed regions. An interpolation between the intensities sampled at intervals and an intensity characteristic as a function of time may be determined that represents a sufficiently good approximation of an intensity characteristic that is acquired if the vessel or the tissue was acquired continuously in the recording geometry.

The interpolation may occur so that an analytic function is determined for the intensity characteristic. However, as the intensity characteristic as a function of time it is also possible to disclose a sequence of discrete intensity values, that, however, includes a higher temporal resolution than the actual recording data for the recording geometry. An interpolated re-sampling may therefore take place.

Due to known recording geometries and the orthogonality of the individual base functions, the volume weighting factors, e.g. the weights that describe the weighting of the base functions for the individual voxels, may be calculated from the projection weighting factors. The projection weighting factors may, for example, describe a weighting of the base functions, by which the respective intensity characteristics as a function of time may be approximated.

The individual projection images may, for example, be acquired after an injection of contrast medium into the examination object, for example into a patient. The acquired intensities in the projection images therefore vary, for example, as a function of a contrast medium concentration in the regions of the examination object that are penetrated by X-rays received in the corresponding imaging region of the detector. The imaging regions may be individual image points of the projection images or regions that are each acquired by a sensor element of the X-ray detector. However, a plurality of the image points or sensor elements may be combined to form larger imaging regions that are processed. The image data of the projection images may describe a radiation intensity acquired directly in the respective imaging region. However, the image data may also describe a variable correlating herewith, for example an attenuation of the X-ray radiation through the penetrated examination object.

The different recording geometries may, for example, correspond to a plurality of recording angles of a rotation or swiveling about a central axis under which the individual projection images are recorded. The rotation or swiveling of the X-ray detector, for example, together with an X-ray source, may occur, for example, by way of a gantry, as is used inter alia in computer tomographs, or a C-arm. An appropriate configuration of a used X-ray device may provide that the individual recording geometries may be optimally exactly reproduced for recording the projection images at different recording times. The projection images may, for example, be recorded so that at least one projection image in each case is acquired in a plurality of successive recording intervals for the plurality of recording geometries, with the recording geometries, under which the recordings are made, are identical for the different recording intervals. The projection images for the different recording geometries may each be recorded in the same order in the individual recording intervals, for example, if the X-ray detector is moved on a circular path around the examination object, or in successive recording intervals in the reverse order respectively, for example if the X-ray detector is swiveled backwards and forwards, for example by a C-arm, around the central axis.

Different interpolation methods may be used to provide the intensity characteristics as a function of time. For example, a linear or polynomial interpolation may be carried out or an interpolation may be carried out with the aid of splines. Interpolation functions may be used that are configured to the base functions used. The projection weighting factors may depend on an integral over a function of the intensity characteristic as a function of time or over the intensity characteristic as a function of time itself. For example, the integral may use Kepler's rule for interpolation and integration.

A cost function may be minimized for each recording geometry in order to determine the projection weighting factors associated with the recording geometry. Imaging differences, on which the cost function depends, are associated with all imaging regions for the respective recording geometry. The imaging differences may be a difference between the intensity characteristic associated with the respective imaging region for the respective recording geometry and a weighted sum of the base functions. The individual base functions in the weighted sum are weighted by the associated projection weighting factors.

The imaging differences are firstly time-dependent. The time dependency may be eliminated, for example, in that the cost function depends on the integrals of the imaging differences or on functions depending on the imaging differences. Alternatively, the total cost function may be integrated over time. For example, the 2-norm, e.g. the Euclidean norm of the imaging differences, may be used as the cost function. The imaging differences d may be calculated by the following formula:

$$d^k(t) = \sum_{i=1}^{I} b_i^k f_i(t) - p^k(t)$$

The index k designates the respective recording geometry here, for which the respective imaging differences d are specified and for which the projection weighting factors b are determined by the minimization of the respective cost function. $f_i(t)$ in each case designates the $i^{th}$ base function. p(t) designates the intensity characteristics of the respective imaging regions. The variables d, b and p are vectorial variables, with the individual entries in the vectors each associated with individual imaging regions in the recording geometry k.

The cost function may be calculated for the imaging geometry k for example as the value of the vector d. The time dependency may be eliminated by integrating the individual imaging differences d or the resulting cost function over time. Methods for minimizing a cost function may be known, for example using a gradient method for determining the projection weighting factors.

The respective projection weighting factor for a particular recording geometry and a particular imaging region and a particular base function may be as a scalar product of the intensity characteristic associated with the imaging region for the recording geometry and the base function. A direct calculation or a low computing intensity solution to the minimization problem may be used. In cases in which the base functions fully span the functional space, an exact solution to the minimization problem results from the calculation. Otherwise, the calculation corresponds to an approximate solution to the minimization problem. The quality of the approximation depends on the chosen base functions. If, empirically determined or motivated base functions are used, a high quality approximation, and therewith reconstruction, may be provided.

The scalar product may be calculated as a scalar product in the $L^2$-space, e.g. the functions may be multiplied by each other and a time integration of the product may be carried out, for example, if the base functions and the intensity characteristic are each present as analytic functions. However, the base function and/or the intensity characteristic may be represented in a time-discrete manner and to carry out a numerical integration during the course of calculation of the scalar product.

The solution to the minimization problem by way of the projection weighting factors calculated for a complete set of base functions may be shown as follows:

The intensity characteristics p(t) as a function of time may be represented in the basis of the base functions $f_i(t)$:

$$p(t) = \sum_{i=1}^{\infty} g_i f_i(t), \text{ where } g_i = \int p(t) f_i(t) dt$$

The representation may be inserted in the imaging difference d(t) described above and therefore in the cost function. In an optimum solution for the projection weighting factors, the derivation of the cost function according to the respective projection weighting factor disappears for each of the projection weighting factors b. The following equation therefore applies to a respective projection weighting factor $b_l$:

$$\frac{\partial}{\partial b_l}[d(t)]^2 = 0$$

By inserting d(t), where, as described above, the p(t) are expressed in the basis of the base functions, and integration over time, owing to the orthogonality of the base functions, leads to the respective projection weighting factor $b_l$ for a particular base function $f_l(t)$ is equal to $g_l$. A projection weighting factor that solves the minimization problem corresponds to the scalar product of the respective base function including the respective intensity characteristic as a function of time.

In an embodiment, the volume weighting factors may be determined by ascertaining an exact or approximate solution to a linear equation system that is composed of a plurality of sub-equation systems. Each of the equation systems is associated with one of the recording geometries and describes a correlation, dependent on the imaging rule, between the projection weighting factors of the respective recording geometry and the volume weighting factors. The sub-equation systems may, for example, include for each of the projection weighting factors associated with the respective recording geometry an equation that describes the correlation between the projection weighting factor and a weighted sum of the volume weighting factors. The weighting factors of the weighted sum are specified by the respective imaging rule, e.g. the respective recording geometry. The resulting problem corresponds to a conventional time-independent reconstruction problem. A number of solutions may be known. For example, the reconstruction problem may be solved by a back projection, e.g., the volume weighting factors may be obtained from the projection weighting factors by a back projection.

The validity of the determination of the volume weighting factors is described below:

The aim of the method is to calculate the intensity characteristic x(t) for the individual voxels of the perfusion data set as a weighted sum of the base functions $f_i(t)$. With the volume weighting factors $a_i$, the following results in a vectorial display:

$$x(t) = \sum_{i=1}^{I} a_i f_i(t)$$

The imaging rule may be represented as a matrix $A^k$ in the notation. The index k in turn refers to the respective recording geometry. The following applies to the imaging rule:

$$A^k x(t) = p^k(t) = \sum_{i=1}^{I} b_i^k f_i(t)$$

Since the equation applies to all times, the equation is also fulfilled when both sides of the equation are multiplied by an individual base function $f_j(t)$ and are then integrated over time. The following equation is obtained:

$$\int A^k \sum_{i=1}^{I} a_i f_i(t) f_j(t) dt = \int \sum_{i=1}^{I} b_i^k f_i(t) f_j(t) dt$$

Since the base functions are orthogonal to each other, the time integral disappears over the product of the base functions in all cases in which the indices i, j are not equal. If the indices are equal, the product of the base functions, if standardized, are equal to 1. The following results for the respective sub-equation system:

$$A^k a_j = b_j^k$$

The vector equation corresponds to a plurality of equations that each describe the correlation of a projection weighting factor b for the respective recording geometry k, the respective base function $f_j$ and a respective recording region having a weighted sum of the volume weighting factors $a_j$ for the individual base functions $f_j(t)$ and the individual voxels.

The volume weighting factors may be calculated a with the aid of recording rules for the individual recording geometries directly from the projection weighting factor b. The scans may be carried out in such a way that the equation system is overdetermined, and the scan data is, moreover, flawed, the corresponding equation system may be approximately solved. In terms of the structure the equation system corresponds to a typical reconstruction problem for time-independent reconstructions of three-dimensional X-ray image data sets. Therefore, known approaches, for example, a back projection, may be used to approximately solve the equation system.

In an embodiment, base functions determined from a specified, empirical function set by a main component analysis may be used as the base functions. For example, Gaussian distribution functions and/or gamma distribution functions may be used as the functions of the empirical function set. Apart from a shift in respect of the time axis, the functions of the empirical function set may be identical to each other.

Gaussian distribution functions or gamma distribution functions describe in an approximation the change over time in the contrast medium concentration at an individual point in the scan volume. Since, however, at different points of the scan volume, vessels or tissue include different spacings from a position, at which the contrast medium is introduced into the vessel or into the tissue, a plurality of corresponding functions shifted in relation to each other in terms of time may be used as the empirical function set.

One drawback of the use of an empirical function set is that a large number of corresponding functions are required for a high time resolution. For example, 25 functions that have been shifted in relation to each other may be used. One drawback of direct use of a corresponding function set is that the functions are not orthogonal to each other, so some of the proposed processing acts may not be applied with direct use of the functions as base functions. Furthermore, use of a large number of base functions may lead to a relatively large number of projection images to be recorded for the individual recording geometries since the number of weights to be calculated also increases proportionally due to the increase in the number of base functions that may lead to a lengthening of the scan time and an increase in radiation exposure for the examination object and that may only be possible if very fast projection image acquisition is possible.

Embodiments provides reducing the empirical function set by applying a main component analysis to a smaller number of orthogonal base functions. For example, six orthogonal base functions may be generated from 25 functions of the empirical function set and be used in the method.

In an embodiment, the time dependency of at least one of the base functions and/or at least one determined voxel of the perfusion data set may include at least one frequency component with a period duration is shorter than twice the interval between two successive projection images acquired in the same recording geometry. According to the Nyquist-Shannon sampling theorem, the frequency bandwidth of a scan is equal to half the sampling frequency. Temporal undersampling may occur.

Empirically motivated base functions prior knowledge about expected properties of the scanning result, for example, about surging and subsiding of a contrast medium concentration in vessels or in the tissue, is used during the course of data evaluation to overcome the limits of the sampling theorem. The base functions change slowly over time and may be constantly differentiated, i.e. are relative smooth. A scanning protocol with relatively few recordings per recording geometry may be used. The relatively smooth base functions may, moreover, lead to a robust reconstruction of the perfusion data set even when relatively few recording geometries are used. Overall, the number of necessary X-ray images for determining the perfusion data set, and therefore the exposure to radiation of the examination object, may be reduced.

An embodiment provides an X-ray device including a controller, an X-ray detector and a moving device for moving the X-ray detector. The controller controls the moving device for moving the X-ray detector into the recording geometries. The projection images may be acquired by the X-ray detector and the perfusion data may be determined from the projection images. The X-ray device may include an X-ray source, that, together with the X-ray detector, may be moved by the moving device. The X-ray detector and/or the X-ray source may be arranged on a gantry or a C-arm or O-arm. The movement between the individual recording geometries may occur as a rotation or swiveling about a central axis.

Embodiments provide a computer program that may be loaded directly into a storage device of a controller of an X-ray device, having programming to carry out the method when the program is run in the controller of the X-ray device.

Embodiments provide an electronically readable data carrier including electronically readable control information stored thereon that includes a computer program and is configured to carry out the method when the data carrier is used in a controller of an X-ray device.

BRIEF DESCRIPTION OF THE FIGURES

FIG. 1 depicts a flow diagram of an embodiment.
FIG. 2 depicts an embodiment of a X-ray device.

DETAILED DESCRIPTION

FIG. 1 depicts a flow diagram for determining a time-dependent, three-dimensional perfusion data set relating to the perfusion of at least one vessel and/or of tissue of an examination object. An X-ray device 1 is used as depicted in FIG. 2. The method subdivides into the recording of a plurality of projection images at acts S1 to S5 and the evaluation of the projection images for determining the perfusion data set at acts S6 to S9.

An individual projection image is recorded at act S1. The examination object is irradiated by an X-ray source 4 with X-ray radiation. The X-ray radiation, that has passed at least partially through the examination object 2, is detected by the X-ray detector 3. The X-ray detector is a pixel detector that for a large number of imaging regions, arranged for example as a matrix, determines an irradiated X-ray intensity during acquisition of the projection image and provides the intensity to the controller 6. At act S2 whether projection images have already been recorded is checked for all recording geometries for which projection images are to be recorded. If the projection images have not been recorded, the recording geometry is altered at act S3. The controller 6 controls a moving device 5, that is depicted in the example as a C-arm, to rotate the X-ray detector 3 and the X-ray source 4 about a central axis 7. A plurality of angles of rotation, for which projection images are to be recorded, may be specified in the form of a scanning protocol. The recording geometry may be set with optimally high precision to provide a high-quality reconstruction. The method from act S1 is repeated after the setting of a further recording geometry.

If, at act S2 projection images have been acquired for all recording geometries, at act S4 whether a sufficient number of recording cycles have been carried out is checked. A minimum number of projection images, that are to be recorded in each of the recording geometries, may be specified by the scanning protocol, for example, as a function of which base functions are used in the framework of the ongoing method. If a sufficient number of projection images has not yet been recorded, the method continues with act S5, in which, in turn, the recording geometry is changed. The moving device may be rotated about the central axis 7. The moving device may be rotated further in act S5 to set a recording geometry present at the start of the method. For example, when using X-ray devices 1 that use a C-arm as the moving device 5, the angles of rotation of the moving device 5 may be limited. The direction of rotation of the moving device 5 may be changed in act S5, so the recording geometries are run through in the reverse order.

If it is determined in act S4 that a sufficiently large number of projection images have been acquired for each of the recording geometries, data recording is terminated and the acquired projection images are evaluated. The evaluation may be carried out by the controller 6. The projection images may be transferred to a separate processing device, for example to a computer. Further processing may be carried out there.

In act S6 intensity characteristics as a function of time are calculated for the respective imaging regions of the X-ray detector 3, for example, the individual pixels. The individual intensity characteristics are associated with exactly one recording geometry respectively here, e.g. only those projection images that were determined in the recording geometry are used for determining a respective intensity characteristic. The intensity characteristic for a respective imaging region may be determined in such a way here that the intensities determined at the different recording times for the imaging region in the recording geometry are temporally interpolated. For example, a polynomial interpolation may be used. Different interpolation methods may be used.

The reconstruction of the perfusion data set from the projection images or from the intensity characteristics derived therefrom take place in the method on the basis of modeling. An empirically based model is used that describes the time characteristic of the intensity for each voxel. The model is parameterized by parameters that are determined from the projection images or from the intensity characteristics determined therefrom. A model is used here in which the intensity characteristic as a function of time for each voxel of the perfusion data set is described by a weighted sum of base functions. The volume weighting factors, that describe the respective weighting for each voxel and each base function, are those parameters that are determined during the course of the evaluation of the projection images.

A reconstruction approach may use prior knowledge about an expected time characteristic of the intensities. Appropriate prior knowledge may be used in that an empirical function set, that includes functions that describe an expected characteristic of a contrast medium concentration at individual voxels, is used as the base function. Appropriate functions may be, for example, Gaussian distribution functions or gamma distribution functions. Since the different relevant points may be at different spacings form a point at which contrast medium is introduced into the vessel or tissue for examination, the empirical function set may be chosen so that the functions are identical, apart from a shift in respect of the time axis.

Direct use of an appropriate function set is disadvantageous for two reasons. First, to attain a high time resolution, a very large number of base functions are used, that may potentially lead to a high number of required recordings for each recording geometry. Second, reconstruction of the perfusion data set is particularly easily possible in the case where all base functions are orthogonal to each other. Therefore, while in the described method, as described, an empirical function set is firstly established, the base functions are determined by way of a main component analysis, so that a relatively low number of orthogonal base functions may be provided. For example, the empirical function set may include 25 Gaussian or gamma distribution functions temporally shifted in relation to each other, from which, for example, six base functions are determined by a main component analysis.

Direct determination of the volume weighting factors from the projection images or the intensity characteristics determined in act S6 is relatively complex. Therefore, in act S7 one projection weighting factor respectively is determined for each recording geometry for each imaging region respectively, e.g., for example for each pixel, and each base function. The projection weighting factor may be determined by calculating a scalar product of the respective base function with the intensity characteristic associated with the respective imaging region. If the base functions and the intensity characteristics are in the form of analytic functions, the scalar product corresponds to multiplication of the functions and subsequent integration over time. The analytic integration may be replaced with a numeric integration, for example if the base function and/or the intensity characteristic are in the form of time-discrete values.

In act S8, the volume weighting factors are calculated from the projection weighting factors. A linear equation system is established that is composed of a plurality of sub-equation systems. Each of the sub-equation systems is associated with a recording geometry and includes for each of the projection weighting factors an equation that describes the correlation between the projection weighting factor and a weighted sum of the volume weighting factors. The weighting factors are specified by the imaging geometry. The imaging rule corresponds to a forward projection, e.g. the projection weighting factors each result according to the equations as a line integral over the volume weighting factors for each voxel, that are implemented by the X-rays that strike in the corresponding imaging region. The weighting of the individual volume weighting factors results directly therefore from the imaging geometry and may therefore be strictly specified or calculated from the imaging geometry.

The resulting equation system may be exactly or approximately solved in order to determine the volume weighting factors. An exact solution is possible, but in the actual scanning mode it is usual, however, for, firstly, more projection images to be recorded than may be used in an ideal model, whereby the equation system is overdetermined. At the same time, the scan data is flawed, however, so an exact solution to the equation system is not usually possible. A large number of options for approximate solution of overdetermined, flawed equation systems may be used, however. For example, the established equation system includes the same structure as conventional static reconstruction problems in the course of three-dimensional X-ray imaging in order to calculate three-dimensional image data sets from a plurality of two-dimensional projection images. All conventional reconstruction methods may be used. In the simplest case, the volume weighting factors may be determined, for example, by a back projection of the projection weighting factors.

In act S9 the perfusion data set is generated, e.g. a weighted sum of the base functions is calculated for each voxel of the perfusion data set, with each base function weighted with the volume weighting factor associated with the respective base function and the respective voxel.

The method may also be implemented in the form of a computer program that implements the method on a controller 6 of an X-ray device when the method is run on the controller 6. Similarly, an electronically readable data carrier (not shown) including electronically readable control information stored thereon may be present, that includes at least one described computer program and is configured in such a way that it carries out the described method when the data carrier is used in the controller 6 of an X-ray device.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for determining a time-dependent, three-dimensional perfusion data set relating to the perfusion of at least one vessel, tissue, or the at least one vessel and the tissue of an examination object, the method comprising:

acquiring projection images of the at least one vessel, the tissue, or the at least one vessel and the tissue in a plurality of recording geometries by an X-ray detector at a plurality of recording times, the acquired projection images describing detected intensities in a plurality of imaging regions of the X-ray detector; determining the three-dimensional perfusion data set, the determining of the three-dimensional perfusion data set comprising associating a weighted sum of specified time-dependent base functions that are orthogonal to each other with each voxel of the three-dimensional perfusion data set, wherein the specified time-dependent base functions are weighted in the respective sum by volume weighting factors that are determined as a function of the projection images;

determining a projection weighting factor for the plurality of imaging regions for each recording geometry and each base function of the specified time-dependent base functions, respectively, wherein the projection weighting factors are determined for a respective recording geometry as a function of intensity characteristics as a function of time for the plurality of imaging regions and of the specified time-dependent base functions;

determining the intensity characteristics, the determining of the intensity characteristics comprising interpolating from the intensities detected in the respective recording geometry at the plurality of recording times in the respective imaging region; and calculating the volume weighting factors as a function of the projection weighting factors of all recording geometries of the plurality of recording geometries and of imaging rules describing the plurality of recording geometries.

2. The method of claim 1, wherein for each recording geometry of the plurality of recording geometries, a cost function is minimized to determine the projection weighting factors associated with the respective recording geometry, wherein for the respective recording geometry, imaging differences, on which the cost function depends, are associated with all imaging regions of the plurality of imaging regions, wherein the imaging differences are differences between the intensity characteristic associated with the respective imaging region for the respective recording geometry and a weighted sum of the specified time-dependent base functions, and wherein the individual base functions in the weighted sum are weighted by the associated projection weighting factors.

3. The method of claim 1, wherein the respective projection weighting factor for a particular recording geometry of the plurality of recording geometries, a particular imaging region of the plurality of imaging regions, and a particular base function of the specified time-dependent base functions is determined as a scalar product of the intensity characteristic associated with the imaging region for the recording geometry and the base function.

4. The method of claim 1, wherein calculating the volume weighting factors comprises ascertaining a solution to a linear equation system that includes a plurality of sub-equation systems, and wherein each sub-equation system of the plurality of sub-equation systems is associated with one recording geometry of the plurality of recording geometries and describes a correlation, dependent on the imaging rule, between the projection weighting factors of the respective recording geometry and the volume weighting factors.

5. The method of claim 4, wherein for each of the projection weighting factors associated with the respective recording geometry, the plurality of sub-equation systems comprise an equation that describes the correlation between the projection weighting factor and a weighted sum of the volume weighting factors, and wherein the weighting factors of the weighted sum are specified by the respective imaging rule.

6. The method of claim 1, wherein base functions determined from a specified, empirical function set by a main component analysis are used as the specified time-dependent base functions.

7. The method of claim 6, wherein functions of the empirical function set use Gaussian distribution functions, gamma distribution functions, or Gaussian distribution functions and gamma distribution functions.

8. The method of claim 7, wherein the functions of the empirical function set are identical to each other apart from a shift with respect to a time axis.

9. The method of claim 1, wherein the time dependency of at least one of the specified time-dependent base functions, at least one voxel of the three-dimensional perfusion data set, or at least one of the specified time-dependent base functions and at least one voxel of the three-dimensional perfusion data set include at least one frequency component with a period duration that is shorter than double an interval between two projection images successively acquired in the same recording geometry.

10. An X-ray device comprising:
an X-ray detector, the X-ray detector configured to acquire a plurality of projection images using a plurality of recording geometries;

a controller, the controller configured to generate a perfusion data set by associating a weighted sum of specified time-dependent base functions, that are orthogonal to each other, with each voxel of the perfusion data set, wherein the base functions are weighted in the respective sum by volume weighting factors that are determined as a function of the plurality of projection images, wherein a projection weighting factor is determined for the imaging regions for each recording geometry of the plurality of recording geometries and each base function respectively, wherein the projection weighting factors are determined for a respective recording geometry as a function of intensity characteristics as a function of time for the imaging regions and of the base functions, wherein the intensity characteristics are determined by interpolation from the intensities detected in the recording geometry at the various recording times in the respective imaging region, according to which the volume weighting factors are calculated as a function of the projection weighting factors of all recording geometries of the plurality of recording geometries and of imaging rules describing the plurality of recording geometries; and a moving device, the moving device configured to move the X-ray detector into the plurality of recording geometries.

11. The X-ray device of claim 10, wherein for each recording geometry of the plurality of recording geometries, a cost function is minimized to determine the projection weighting factors associated with the respective recording geometry, wherein for the respective recording geometry, imaging differences, on which the cost function depends, are associated with all imaging regions of the plurality of imaging regions, wherein the imaging differences are differences between the intensity characteristic associated with the respective imaging region for the respective recording geometry and a weighted sum of the specified time-dependent base functions, and wherein the individual base functions in the weighted sum are weighted by the associated projection weighting factors.

12. A computer program product for determining a time-dependent, three-dimensional perfusion data set relating to the perfusion of at least one vessel, tissue, or the at least one vessel and the tissue of an examination object, the computer program product comprising a non-transitory computer readable storage medium, the non-transitory computer readable storage medium storing computer program codes that comprise instructions executable by at least one processor for performing:

acquiring projection images of the at least one vessel, the tissue, or the at least one vessel and the tissue in a plurality of recording geometries by an X-ray detector at a plurality of recording times, the acquired projection images describing detected intensities in a plurality of imaging regions of the X-ray detector; determining the three-dimensional perfusion data set, the determining of the three-dimensional perfusion data set comprising associating a weighted sum of specified time-dependent base functions that are orthogonal to each other with each voxel of the three-dimensional perfusion data set, wherein the specified time-dependent base functions are weighted in the respective sum by volume weighting factors that are determined as a function of the projection images;

determining a projection weighting factor for the plurality of imaging regions for each recording geometry and each base function of the specified time-dependent base functions, respectively, wherein the projection weighting factors are determined for a respective recording geometry as a function of intensity characteristics as a function of time for the plurality of imaging regions and of the specified time-dependent base functions;

determining the intensity characteristics, the determining of the intensity characteristics comprising interpolating from the intensities detected in the respective recording geometry at the plurality of recording times in the respective imaging region; and calculating the volume weighting factors as a function of the projection weighting factors of all recording geometries of the plurality of recording geometries and of imaging rules describing the plurality of recording geometries.

13. The computer program product of claim 12, wherein for each recording geometry of the plurality of recording geometries, a cost function is minimized to determine the projection weighting factors associated with the respective recording geometry, wherein for the respective recording geometry, imaging differences, on which the cost function depends, are associated with all imaging regions of the plurality of imaging regions, wherein the imaging differences are differences between the intensity characteristic associated with the respective imaging region for the respective recording geometry and a weighted sum of the specified time-dependent base functions, and wherein the individual base functions in the weighted sum are weighted by the associated projection weighting factors.

14. The computer program product of claim 12, wherein the respective projection weighting factor for a particular recording geometry of the plurality of recording geometries, a particular imaging region of the plurality of imaging regions, and a particular base function of the specified time-dependent base functions is determined as a scalar product of the intensity characteristic associated with the imaging region for the recording geometry and the base function.

15. The computer program product of claim 12, wherein calculating the volume weighting factors comprises ascertaining a solution to a linear equation system that includes a plurality of sub-equation systems, and wherein each sub-equation system of the plurality of sub-equation systems is associated with one recording geometry of the plurality of recording geometries and describes a correlation, dependent on the imaging rule, between the projection weighting factors of the respective recording geometry and the volume weighting factors.

16. The computer program product of claim 15, wherein for each of the projection weighting factors associated with the respective recording geometry, the plurality of sub-equation systems comprise an equation that describes the correlation between the projection weighting factor and a weighted sum of the volume weighting factors, and wherein the weighting factors of the weighted sum are specified by the respective imaging rule.

17. The computer program product of claim 12, wherein base functions determined from a specified, empirical function set by a main component analysis are used as the specified time-dependent base functions.

18. The computer program product of claim 17, wherein functions of the empirical function set use Gaussian distribution functions, gamma distribution functions, or Gaussian distribution functions and gamma distribution functions.

19. The computer program product of claim 18, wherein the functions of the empirical function set are identical to each other apart from a shift with respect to a time axis.

20. The computer program product of claim 12, wherein the time dependency of at least one of the specified time-dependent base functions, at least one voxel of the three-dimensional perfusion data set, or at least one of the specified time-dependent base functions and at least one voxel of the three-dimensional perfusion data set include at least one frequency component with a period duration that is shorter than double an interval between two projection images successively acquired in the same recording geometry.

* * * * *